United States Patent [19]

Crossett et al.

[11] 4,201,215
[45] May 6, 1980

[54] APPARATUS AND METHOD FOR CLOSING A SEVERED STERNUM

[76] Inventors: E. S. Crossett, 1501 Arizona Ave., El Paso, Tex. 79902; Willard L. McCormick, 4906 Souther SE., Albuquerque, N. Mex. 87100

[21] Appl. No.: 830,567

[22] Filed: Sep. 6, 1977

[51] Int. Cl.$^2$ .......................................... A61B 17/08
[52] U.S. Cl. ................................... 128/335; 128/346; 128/92 EA; 24/88; 24/263 R
[58] Field of Search .............. 128/334 R, 334 C, 335, 128/336, 337, 346, 92 B, 92 D, 92 EA; 24/87 R, 88 R, 115 A, 263 R

[56] References Cited

U.S. PATENT DOCUMENTS

| | | | |
|---|---|---|---|
| 268,632 | 12/1882 | Danforth | 128/337 |
| 380,093 | 3/1888 | Cruice et al. | 128/336 |
| 1,803,084 | 4/1931 | Wiziarde et al. | 24/263 R |
| 3,385,299 | 5/1968 | Le Roy | 128/337 |
| 3,802,438 | 4/1974 | Wolvek | 128/335 |
| 3,857,396 | 12/1974 | Harwick | 128/335 |

FOREIGN PATENT DOCUMENTS 752633 7/1933 France ...................................... 128/337

*Primary Examiner*—Dalton L. Truluck
*Attorney, Agent, or Firm*—Larson, Taylor and Hinds

[57] ABSTRACT

A sternum clamp is provided which comprises a first elongate planar clamping member having turned over, opposed lateral flanges defining guide groove members slidingly received in said guide grooves and movable longitudinally relative to the first clamping member. The clamping members each include pairs of opposed clamping hooks for engaging the opposite sides of a severed sternum. The spacing between the pairs of hooks enables the clamping members to be engaged with the opposed jaws of a pair of pliers to thereby tighten the engagement between the clamping members. The sternum clamp is fabricated of a material such that when the lateral flanges are crimped, the second clamping member is lockingly retained by these flanges. In a method for closing a severed sternum with the sternum clamp, the following steps are carried out: drawing the severed sternum together; burning opposed, matching pairs of holes through each side of the severed sternum; pushing the hooks of one clamping member through one of the pairs of holes and the hooks of the clamping member through the other pair of holes; pushing the clamping members further into engagement until the severed sides of the sternum are correctly positioned; and crimping the lateral flanges to lock the clamping members together.

11 Claims, 11 Drawing Figures

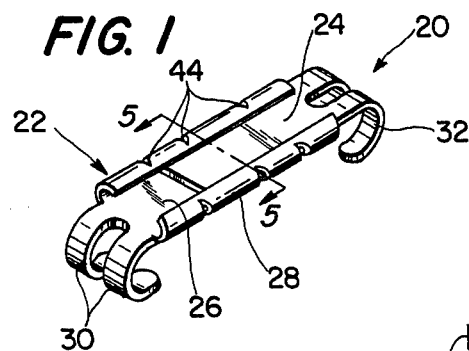
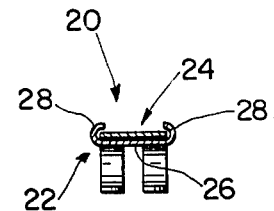
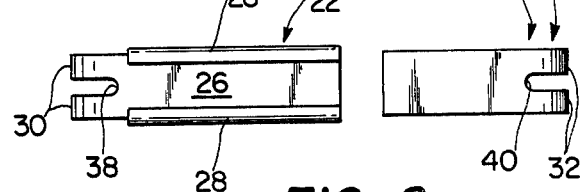
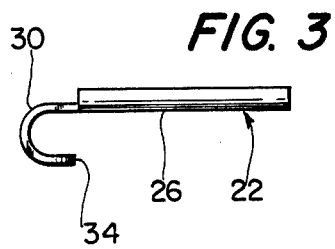
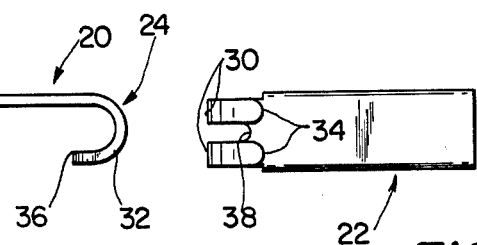
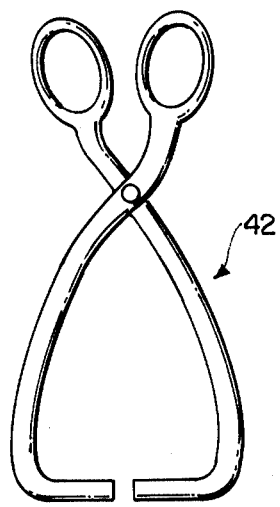
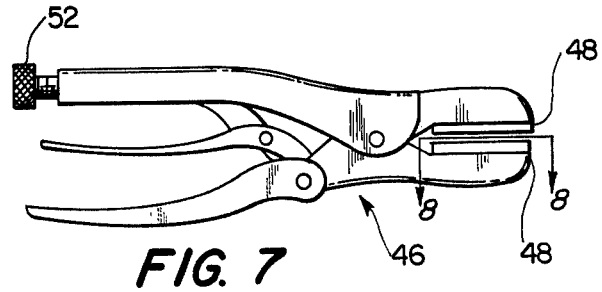
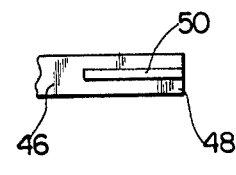

APPARATUS AND METHOD FOR CLOSING A SEVERED STERNUM

BACKGROUND OF THE INVENTION

1. Field of the Invention

This invention relates to sternum clamping device and a method for using the device to close a severed sternum.

2. Description of the Prior Art

In accordance with a typical method presently in use, upwards of forty-five minutes is required to close a severed sternum following major chest surgery. This conventional procedure of closing a severed sternum involves the use of three suture wires and a metal band, which suture wires are slipped through matching holes burned with a hot wire on each side of the severed sternum through a portion of the cartilage of the sternum located between the ribs. The severed sternum is then closed, with the wires being brought together in front of the closed sternum, twisted together, and snipped above the twist. The band is then tightened about the sternum and fastened with a lever device much like that used in a package banding machine.

Aside from the inherent disadvantages of substantially prolonging an already complex and traumatic chest operation, the sternum closing technique described above suffers other important disadvantages. For example, it is not possible with this technique to select the appropriate tension necessary to hold the sternum together and thus it sometimes happens that the portions of the severed sternum which have been brought together slip out of proper alignment. More generally, this technique can also cause further bleeding and result in macerative damage to the cartilage and associated muscle tissue with a consequent increase in postoperative discomfort suffered by the patient and in the time required for healing. Further such clamps cannot be easily removed should internal bleeding and/or patient discomfort so require.

There are, of course, a variety of general purpose surgical clamps presently known in the art. Among these are the surgical clamps and like devices disclosed in U.S. Pat. Nos. 268,632 (Danforth); 2,472,009 (Gardner); 3,068,869 (Shelden et al); 3,601,127 (Finegold); and 3,951,138 (Akopov), although this listing is, of course, in no way exhaustive. Generally speaking, these clamps are not intended for use with, or suitable for use in, closing the sternum and do not provide the advantages of the sternum clamping device of the invention.

SUMMARY OF THE INVENTION

According to the present invention, a sternum clamp is provided which overcomes the disadvantages associated with the prior art devices. In a preferred embodiment of the invention, the sternum clamp comprises a first clamping member including an elongate planar body portion and turned over, opposed lateral flanges defining a pair of longitudinally extending recesses or guide grooves, and a second elongate planar clamping member which is received in the guide grooves of the first clamping member so as to overlie at least a portion of the body portion of the latter. The clamping hook members each include a pair of hooks located at one end thereon for engaging the opposed sides of the severed sternum. The spacing between the pairs of hooks provided an advantageous location for enabling the clamping members to be engaged by a pair of the opposed jaws of a pair of pliers, the pliers serving to push the clamping members into tighter engagement after the opposed sides of the severed tissue have been engaged by the hooks.

The sternum clamp is fabricated of a material such that when the turned over lateral flanges of the first member are crimped about the second clamping member, that the latter is lockingly retained. Advantageously, the sternum clamp is comprised of metal which has a transverse grain.

In one embodiment, wherein crimping is not required, one of the clamping members is provided with at least one boss and the other clamping member is provided with at least one recess for receiving the boss so as to provide locking engagement between the two clamping members.

In accordance with a further aspect of the invention, a method is provided for closing a severed sternum with a sternum clamp. The clamp used corresponds to that described above and the method includes the steps of drawing the severed sternum together; burning opposed and matching holes through each side of the severed cartilage of the sternum; inserting the hooks of the first and second clamping members through opposed holes; tightening the engagement between the clamping members so that the severed sides of the cartilage are positioned so as to close the opening; and crimping the turned over lateral flanges of the first clamping member so as to lock the clamping members in place.

The apparatus and method of the invention provide for the rapid closure of a severed sternum while reducing the bleeding and the macerative damage to cartilage and muscle tissue, and causing less patient discomfort than is associated with prior art techniques. Further, the surgical clamp can be quickly removed should internal bleeding and/or patient discomfort so require. In addition, the sternum clamp provides the appropriate tension on the sternum while avoiding slippage, relative to the sternum, once in position.

Additional features and advantages of the invention will be set forth in or apparent from, the detailed description of a preferred embodiment found hereinbelow.

BRIEF DESCRIPTION OF THE DRAWINGS

FIG. 1 is a perspective view of the sternum clamp of the invention;

FIG. 2 is a plan view of the sternum clamp depicted in FIG. 1 with the parts separated;

FIG. 3 is a side elevational view of the sternum clamp of FIG. 2;

FIG. 4 is a bottom plan view of the sternum clamp of FIG. 2;

FIG. 5 is a transverse cross-sectional view, taken generally along the lines 5—5 in FIG. 1;

FIG. 6 is a plan view of a pair of pliers which can be used in tightening the clamp of the invention;

FIG. 7 is a plan view of a pair of vise grip pliers suitable for crimping the clamp of the invention;

FIG. 8 is a cross-sectional view taken generally along line 8—8 in FIG. 7;

DETAILED DESCRIPTION OF THE PREFERRED EMBODIMENT

Figure 9:
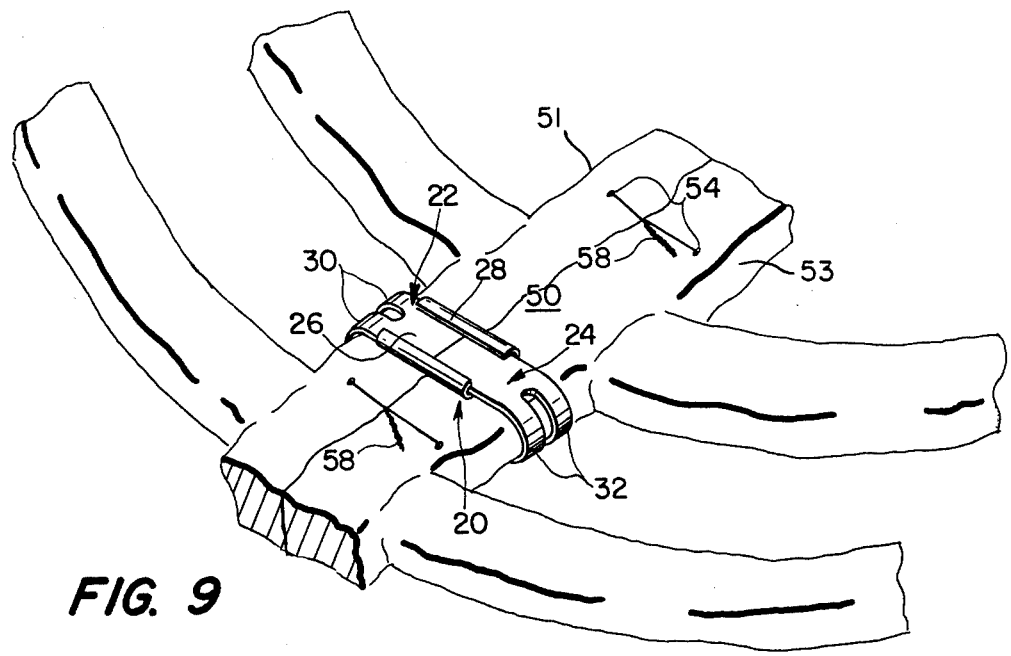
FIg. 9 is a perspective view of the sternum clamp of the invention positioned on the sternum.

With reference to the drawings, and in particular to FIGS. 1, 2, 3, 4, and 5, there is depicted a preferred embodiment of the sternum clamp of the invention. The clamp, is generally denoted 20, basically comprises a first clamping member 22 and a second clamping member 24, the latter being received in the former, as shown in FIG. 1 and described in more detail hereinbelow.

The first clamping member 22 is as best seen in FIGS. 2, 3, and 4, includes an elongate planar body portion 26 with turned over, opposed, lateral flanges 28 (see FIGS. 2, 3, and 5), the second clamping member 24 being friction fit between planar body portion 26 and turned over lateral flanges 28. Clamping member 22 further includes a pair of semicircular hooks or tines 30 which are formed integrally with and extended from the end of elongate planar body portion 26 opposite that which engages clamping member 24. Clamping member 24 includes a similar pair of hooks 32. Owing to the curvature of hooks 30 and 32, the semi-blunted tips of hooks 30 and 32, denoted 34 and 36, respectively, are directed toward each other as illustrated in FIG. 3.

The individual hooks of hook pairs 30 and 32 are spaced apart so as to define therebetween, adjacent the bases thereof, respective end edges or edge portions 38 and 40 of clamping members 22 and 24 (see FIGS. 2 and 4). These portions 38 and 40 are adapted to permit the opposed jaws of a pair of pliers, such as shown at 42 in FIG. 6, to engage clamping members 22 and 24 therebetween. Thus, with the pliers so engaged, closing of such pliers will cause tightening of the engagement between clamping members 22 and 24. It would be appreciated that although the pliers depicted in FIG. 6 have elongated, curved and opposed jaws, other pliers, e.g., needle nose pliers, or other similar devices, can be used for the purpose in question.

In a preferred embodiment, clamping members 22, 24 of clamp 20 are fabricated of 32 mil 316 stainless steel with the grain running transverse to longitudinal axis of the clamp. For medical applications, and especially when implantation is involved, stainless steel is a desirable material, as it is strong and does not for the most part interact harmfully with the body tissue. Further, it is comtemplated that when finally positioned, the clamp 20 will be crimped as described below about clamping member 24 as indicated by opposed pairs of crimp marks 44 (FIG. 1). The transverse grain greatly facilitates this crimping step.

Considering the crimping step, and referring to FIG. 7, a suitable pair of crimpers, denoted 46, are illustrated. Crimpers 46 comprises vise-grip pliers which are modified by securing a plate 48 with a single ridge 50 on each face of the pliers (see FIG. 8). Further, it is desirable that the pliers be preset for maximun closure so that the degree of crimping is controlled. Such maximum closure can be present by the use of an adjustment screw 52.

A method for closing a sternum which has been longitudinally severed for the purposes of major chest surgery will now be described in connection with FIG. 9. As a first step, the two severed pieces 51 and 53 of cartilage of the sternum are drawn together. This is accomplished by burning opposed, matching holes 54 in each side of the cartilage with a hot wire. A retaining wire 58 is then threaded through the holes 54 and the ends thereof pulled together in front of the sternum, thereby closing together the severed sternum. The wires 56 are twisted together and snipped off above the twist. The twisted section is then bent down parallel to the rest of the wire (as shown in FIG. 9) so as not to entangle any body tissue. It is noted that depending on the circumstances, one or more of the wires 58 can be used. This portion of the procedure is similar to the prior art techniques described above.

As a next step, an additional pair of holes is burned through each adjacent edge of the cartilage of the sternum and hooks 30 and 32 are pushed through respective pairs of these holes. It is noted that, if necessary, the curvature of hooks 30 and 32 can be changed with, for example, a needle holder to accommodate variations in sternum taper and thickness. It is also noted that the second clamping member 24 can be slid into the first clamping member 22 either before or after hooks 30 and 32 are inserted into the sternum, depending on the circumstances.

After clamp 20 is fit around the sternum, the jaws of a pair of pliers such as shown in FIG. 6 are brought into engagement with the end edge portions 38 and 40 of clamping members 22 and 24, respectively, the jaws then being closed to further advance member 24 into member 22 until the severed sides or edges of the sternum are appropriately positioned with respect to each other. It is noted that because turned over lateral edges 28 are on the side of clamp 20 opposite to the sternum, the edges 28 of the clamp will not become fouled in sternum tissue as members 20 and 22 are brought together. To provide crimping, the jaws of crimpers 46 corresponding to crimpers of FIGS. 7 and 8 are placed adjacent the turned over lateral edges 28 of clamping member 22 and the edges 28 are crimped several times, as indicated in FIG. 1. This results in the clamping members 22 and 24 being bowed slightly, so as to lock the members together.

It will be appreciated that a plurality of clamps 20 can be used to close a severed sternum if required. Moreover, wires 58 can be removed as desired, preparatory to suturing the skin tissue above the sternum. Following surgery, as necessary, a clamp 20 can be easily removed by making a superficial incision above the sternum and then bending hooks 30 and 32 upwardly with a needle holder. It is also noted that a sternum clamp 20 can be used to realign ribs spread during major chest surgery. In such a use, the hooks 30 and 32 are placed about each of a pair of spread ribs and the clamping members 22, 24 brought into engagement and crimped in the manner previously described.

It is further noted that an operation for closing the sternum utilizing the method of the invention can be accomplished in an average of six minutes or less, which is, of course, less than the approximately forty-five minutes required by the prior art method discussed hereinabove.

Figure 10:
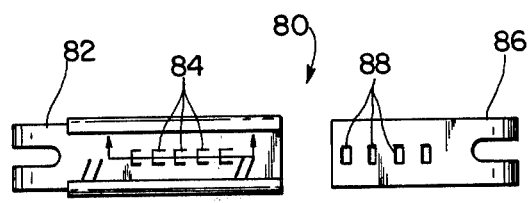
FIG. 10 is a top plan view of an alternate embodiment of the sternum clamp of the invention.
Figure 11:
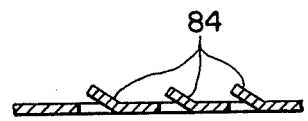
FIG. 11 is a longitudinal cross-section view taken generally along line 11—11 of FIG. 10.

An alternate embodiment of the clamp of the invention is depicted in FIG. 10. The sternum clamp, which is generally denoted 80, is identical to the clamp described above except that clamp 80 includes a first clamping member 82 with a plurality of linearly spaced punched-out tongues or bosses 84 (see FIGS. 10 and 11), the second clamping member 86 includes a plurality of linearly spaced recesses 88 which are adapted to accept and engage tongues 84. Clamp 80 can be used to close a severed sternum in much the same way as the clamp described previously. Thus, as the second clamping member 86 is pushed into engagement with the first clamping member 82, recesses 88 are engaged and retained by tongues 84 to provide locking of clamping member 82 and 86. Clamping member 82 can then be crimped as previously discussed, as desired. However, it is noted, as compared to clamp 20 of FIGS. 1 to 5, clamp 88 requires more strength to change the positioning of the clamping members 82, 86 due to the greater friction caused by the protruding bosses 84. Further the positioning of clamping members 82, 86 cannot be set with the same precision due to the preset nature of the positions of bosses 84 and recesses 88.

Although the present invention has been described relative to exemplary embodiments thereof, modifications and variations can be effected in these embodiments without departing from the scope and spirit of the invention.

We claim:

1. A sternum clamp comprising:
a first elongate clamp member including a substantially planar body portion and turned over flange portions on opposite sides thereof defining a pair of longitudinally extending recesses; and
a second elongate clamp member including a substantially planar body portion slidingly received in the recesses of said first clamp member so as to overlie at least a part of the body portion of said first clamp member;
said first and second clamp members each including a pair of clamping hooks at one end thereof, said pairs of clamping hooks, in use, engaging opposed sides of the severed sternum, and each of said pairs of clamping hooks being spaced apart to define means for enabling engagement with the respective jaws of a pair of pliers so that the two members can be brought into tighter engagement when said clamping hooks are in place in the sternum, said hooks being generally U-shaped in cross-section, the free ends of the U-shaped hook lying in a plane substantially parallel to the planes of the planar body portions of said first and second clamp members and being rounded at the tips thereof, said clamping members being fabricated of stainless steel having a grain which extends transversely to the longitudinal axis of the clamping members.

2. A suture clamp in accordance with claim 1 wherein said second clamping member is friction fitted into said first clamping member.

3. A suture clamp in accordance with claim 1 wherein said planar body portion of said first clamping member is provided with at least one boss and said second clamping member is provided with at least one recess for receiving said boss to provide locking engagement of the clamping members.

4. A method for closing a severed sternum with a sternum clamp comprising a first elongate clamp member including a substantially planar body portion and turned over, lateral flange portions defining a pair of longitudinally extending recesses; and a second elongate clamp member including a substantially planar body portion slidingly received in the recess of said first clamp member so as to overlie at least a part of the body portion of said first clamp member; said first and second clamp members each including at least one clamping hook at one end thereof, said method comprising the steps of:
drawing the severed sternum together;
providing a pair of opposed aligned holes through the adjacent portions of the severed sternum;
pushing the at least one hook of the first clamping member through one of the holes, and the at least one hook of the second clamping member through the other hole;
using forces exerted at the opposite ends of the clamp to bring said clamping members into engagement such that the severed portions of the sternum are positioned with respect to each other so as to close the sternum; and
crimping the turned over, lateral flanges of the first clamping member so as to lock the clamping members in engagement.

5. A method in accordance with claim 4 wherein a plurality of said sternum clamps are used in closing the sternum.

6. A method in accordance with claim 4 wherein the step of providing a pair of aligned holes comprises placing a hot wire in contact with the cartilage of the sternum and pushing the hot wire into the cartilage.

7. A method in accordance with claim 4 including the step of providing a pair of aligned holes comprising buring the holes into a portion of the sternum located between the ribs.

8. A method in accordance with claim 4 including adjusting the curvature of the clamping hooks to accommodate the holes provided in the sternum.

9. A method in accordance with claim 4 wherein the step of drawing the severed sternum together includes the steps of:
burning opposed, matching holes through each side of the cartilage of the severed sternum;
threading wire through the holes;
bringing the wire together in front of the sternum so as to close up the severed sternum;
twisting the wires together; and
snipping the wires above the twist.

10. A method in accordance with claim 4 wherein the step of bringing the clamping members into engagement includes the steps of gripping the opposite ends of the clamp with the jaws of a pair of pliers and closing the jaws of the pliers to bring the clamping members into tighter engagement and wherein the step of crimping the lateral flanges of said first clamping member includes the steps of placing said lateral flanges between the jaws of a pair of crimping pliers having a central crimping ridge thereon and closing the jaws of the crimping pliers to a preset limit.

11. A method in accordance with claim 4 wherein said clamping members each include a pair of clamping hooks at the said one end thereof and said step of bringing said clamping members into engagement comprises gripping said clamping members between the pairs of clamping hooks with the jaws of a pair of pliers.

* * * * *